United States Patent [19]

Engelhart et al.

[11] 4,442,122
[45] Apr. 10, 1984

[54] 1,2-DIBROMO-2-CYANOALKANE ANTIMICROBIAL COMPOUNDS

[75] Inventors: John E. Engelhart, Westfield; Marshall R. Angeles, Scotchplains, both of N.J.; Michael J. D'Errico, Flossmoor, Ill.

[73] Assignee: Merck & Co., Inc., Rahway, N.J.

[21] Appl. No.: 333,276

[22] Filed: Dec. 22, 1981

[51] Int. Cl.³ .................. C07C 121/16; C07C 121/46; A01N 37/34
[52] U.S. Cl. ........................................ 424/304; 71/67; 260/464; 260/465.7; 544/402; 546/246; 548/214; 548/215; 548/240; 548/300; 548/372; 548/566; 549/74; 549/491
[58] Field of Search .................. 260/465.7, 464; 71/67; 424/304

[56] References Cited

U.S. PATENT DOCUMENTS

| | | | |
|---|---|---|---|
| 3,608,084 | 9/1971 | Matt | 424/304 |
| 3,833,731 | 9/1974 | Grier et al. | 424/304 |
| 3,873,597 | 3/1975 | Harmetz et al. | 260/465.7 |
| 3,877,922 | 4/1975 | Grier et al. | 71/67 |

FOREIGN PATENT DOCUMENTS 1424943 2/1976 United Kingdom .

OTHER PUBLICATIONS

Gershon, et al., J. Med. Chem. 20(4), 606–9, (1977).

*Primary Examiner*—Joseph Paul Brust
*Attorney, Agent, or Firm*—Raymond M. Speer; Alice O. Robertson; R. Brent Olson

[57] ABSTRACT

Antimicrobial compounds of the formula:

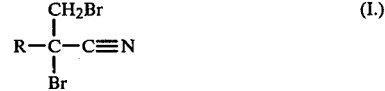

(I.)

where
R is $C_{3-12}$alkyl, straight or branched chain $C_3$–$C_8$ cycloalkyl; $C_{3-8}$cycloalkyl$C_{1-3}$alkyl; or saturated heterocyclic radical selected from the group consisting of pyrrolidinyl, tetrahydrofuranyl, tetrahydrothienyl, isoxazolidinyl, oxazolidinyl, isothiazolidinyl, pyrazolidinyl, imidazolidinyl, piperazinyl, and piperidinyl.

10 Claims, No Drawings

1,2-DIBROMO-2-CYANOALKANE ANTIMICROBIAL COMPOUNDS

BACKGROUND OF THE INVENTION

1. Field of the Invention

The present invention is concerned with novel compounds which are 1,2-dibromo-2-cyanoalkanes. The present invention is also concerned with antimicrobial compositions containing these novel compounds as active ingredients, as well as with a method of inhibiting the growth of bacteria, yeast, fungi, and algae by contacting said bacteria, yeast, fungi, and algae with the novel compounds of the present invention. These novel antimicrobial compounds have a number of important industrial and agricultural applications.

As used herein, the term "antimicrobial" describes the killing of, as well as the inhibition of or control of the growth of bacteria, yeasts, fungi, and algae. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications include: inhibiting the growth of bacteria in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; as a hard surface disinfectant to prevent growth of bacteria and fungi on walls, floors, etc.; and in swimming pools to prevent algae. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

A particular application for which the antimicrobial compounds of the present invention have been found especially useful is in the protection of paint films from attack by fungi. Paint film fungicides which can preserve paint films from the deleterious effects of fungal attack which occur during weathering of the paint film have long been sought. Few, however, have been found due to the stringent requirements for such a successful paint film fungicide. Moreover, the ability to provide in-can preservative activity, as well as paint film protection, is also desirable. However, this additional characteristic is seldom seen in a paint film fungicide.

Antimicrobial compounds are also utilized for agricultural applications, for example in preventing or minimizing the growth of harmful bacterial, yeast, and/or fungi on plants, trees, fruit, seeds, or soil.

2. Brief Description of the Prior Art

Matt U.S. Pat. No. 3,608,084 describes halogenated aliphatic nitriles for controlling the growth of aerobacter bacteria in industrial water systems.

Grier, et. al., U.S. Pat. Nos. 3,833,731 and 3,877,922; and Harmetz, et. al. U.S. Pat. No. 3,873,597 describe 2-bromo-2-bromomethylglutaronitrile and related compounds and their use as antibacterial, antifungal, and algicidal agents.

Gershon, et. al., in J. Med. Chem. 20(4), 606-9 (1977), describe the antifungal properties of 2-bromo-3-fluorosuccinic acid esters.

Radar et al, British Pat. Spec. No. 1,424,943 describes α-(halomethyl)mandelonitrile microbiocides.

However, there is no suggestion in any of the above references of the particular alkyl compounds of the present invention or their broad spectrum of antimicrobial activity.

DETAILED DESCRIPTION OF THE INVENTION AND PREFERRED EMBODIMENTS

In accordance with the present invention there are provided novel 1,2-dibromo-2-cyanoalkanes of the formula:

(I.)

where
R is $C_{3-12}$alkyl, straight or branched chain; $C_3$–$C_8$ cycloalkyl; $C_{3-8}$cycloalkyl$C_{1-3}$alkyl; or saturated heterocyclic radical selected from the group consisting of pyrrolidinyl, tetrahydrofuranyl, tetrahydrothienyl, isoxazolidinyl, oxazolidinyl, isothiazolidinyl, pyrazolidinyl, imidazolidinyl, piperazinyl, and piperidinyl.

Particularly preferred compounds of the present invention are the following:
1,2-dibromo-2-cyanopentane;
1,2-dibromo-2-cyano-3-methylbutane;
1,2-dibromo-2-cyanohexane;
1,2-dibromo-2-cyano-3,3-dimethylbutane;
1,2-dibromo-2-cyanononane;
1,2-dibromo-2-cyanoundecane;
1,2-dibromo-2-cyano-2-cyclopropylethane;
1,2-dibromo-2-cyano-3-cyclohexylpropane;
1,2-dibromo-2-cyano-4-cyclooctylbutane.

In accordance with the present invention there is further provided an antimicrobial composition comprising a carrier and an antimicrobially effective amount of a compound of the formula:

(I.)

where
R is $C_{3-12}$alkyl, straight or branched chain; $C_3$–$C_8$ cycloalkyl; $C_{3-8}$cycloalkyl$C_{1-3}$alkyl; or saturated heterocyclic radical selected from the group consisting of pyrrolidinyl, tetrahydrofuranyl, tetrahydrothienyl, isoxazolidinyl, oxazolidinyl, isothiazolidinyl, pyrazolidinyl, imidazolidinyl, piperazinyl, and piperidinyl.

The 1,2-dibromo-2-cyanoalkane active ingredient of the antimicrobial composition of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the 1,2-dibromo-2-cyanoalkane is liquid, it may be employed neat or may be incorporated into various formulations, both solid and liquid, as an adsorbate on suitable inert carriers such as talc, clays, diatomaceous earth and the like.

Thus, it will be appreciated that the 1,2-dibromo-2-cyanoalkanes may be employed to form antimicrobial formulations containing such compounds as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as loweralkanols, kerosene, benzene, toluene and other petroleum distillate fractions or mixtures thereof.

It will be understood also that the 1,2-dibromo-2-cyanoalkane active ingredients may be used in combination one with the other as well as with other antimicrobial materials. For example, these compounds can be combined with other fungicides and bactericides such as 2-(4'-thiazolyl)-benzimidazole, sorbic acid, propionic acid, mycostatin, sodium diacetate, trichomycin, amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, sodium benzoate in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations. It is quite clear also that the 1,2-dibromo-2-cyanoalkanes can be combined with other algicidal agents such as benzalkonium chlorides and other quaternary ammonium compounds to obtain formulations particularly suitable to special problems of algae control.

In accordance with the present invention there is still further provided a method of inhibiting the growth of at least one of: bacteria, yeast, fungi, and algae, comprising contacting said bacteria, yeast, fungi, or algae, with a bactericidally, fungicidally, or algicidally effective amount of a compound of the formula:

where
is $C_{3-12}$alkyl, straight or branched chain; $C_3$–$C_8$ cycloalkyl; $C_{3-8}$cycloalkyl$C_{1-3}$alkyl; or saturated heterocyclic radical selected from the group consisting of pyrrolidinyl, tetrahydrofuranyl, tetrahydrothienyl, isoxazolidinyl, oxazolidinyl, isothiazolidinyl, pyrazolidinyl, imidazolidinyl, piperazinyl, and piperidinyl.

As noted above, the instant invention is based upon the discovery that the 1,2-dibromo-2-cyanoalkanes described above are effective in controlling the growth of bacteria, yeast, fungi and algae in a variety of industrial and agricultural applications. It has been found, for example, that these compounds are effective antimicrobials for the destruction or control of soil fungi and bacteria and for the protection of seeds, bulbs and plants. Also, they are effective algicides in the treatment of pools and ponds, cooling water systems and the like. The utility of the 1,2-dibromo-2-cyanoalkanes of this invention is shown not only by their activity against bacteria and fungi responsible for stunting growth, and even destruction of many types of crop-producing plants, but also for those causing degradation and deterioration of many types of industrial products including, for example, paper, leather, textiles, aqueous systems such as adhesives, resins, drilling fluids, pigment dispersions and latex paints and oleoresinous coatings whose films are particularly vulnerable to the destructive action of fungi. The large economic losses encountered in paper-making operations caused by the accumulation of bacterial and fungal slimes in various parts of the system can be eliminated to a significant extent by use of the compounds described herein.

Thus, for pulp and paper mill systems, there is provided a method of inhibiting the growth of slime-forming bacteria, fungi, and algae, usually encountered in pulp and paper mill systems, comprising incorporating into the mass of fiber and water in such a pulp and paper mill system so as to contact said bacteria, fungi, and algae, at least a bactericidally, fungicidally, and algicidally effective amount of a compound of the formula:

where
R is $C_{3-12}$alkyl, straight or branched chain; $C_3$–$C_8$ cycloalkyl; $C_{3-8}$cycloalkyl$C_{1-3}$alkyl; or saturated heterocyclic radical selected from the group consisting of pyrrolidinyl, tetrahydrofuranyl, tetrahydrothienyl, isoxazolidinyl, oxazolidinyl, isothiazolidinyl, pyrazolidinyl, imidazolidinyl, piperazinyl, and piperidinyl.

The antimicrobial activity of the compounds described above has been confirmed using standard laboratory techniques. They have been found effective, for example, in inhibiting bacteria including Aerobacter sp. such as *A. aerogenes*, Pseudomonas sp. such as *P. aeruginosa*. They have been found effective also against fungi including Aspergillus sp. such as *A. niger*, Pullularia sp. such as *P. pullulans*, Penicillium sp. such as *P. funiculosum*, Alternaria sp. such as *A. brassicicola*, and Saccharomyces sp. such as *S. cerevisiae*. Such bacteria and/or fungi commonly are found on cereal and grain products, on oils, on fruits and vegetables and on cosmetics, leather, electrical insulation, textiles and numerous other materials capable of supporting their growth. Also, such bacteria and/or fungi may be found on plants, seeds, fur and wood and in soils. Further, they may be used to control overgrowth of algae such as Chlorella sp. including *C. pyrenoidosa*

As noted above, it has been found that growth of various harmful fungi and bacteria existing in soil is eliminated or limited by use of formulations containing the 1,2-dibromo-2-cyanoalkanes described herein. The term, soil, as used here is intended to include all media capable of supporting growth of plants and may include humas, sand, manure, compost, artificially created plant growth solutions and the like.

The 1,2-dibromo-2-cyanoalkanes described above have activity against bacteria, yeast, fungi, and algae when employed at appropriate levels of concentration and may be used to inhibit growth of these organisms. It will be obvious to those skilled in the art that the required effective concentration will vary with particular organisms and in particular applications. In general, however, effective fungicidal, bactericidal and algicidal response is obtained when the 1,2-dibromo-2-cyanoalkanes are employed in concentrations ranging between 0.5 and 5000 ppm (parts per million).

For latex plants, latex emulsions and adhesives, amounts of from 100 to 2000 ppm of a compound of the present invention are added during manufacture of the paint, emulsion, or adhesive in order to protect the system during in-can storage against bacteria, fungi, and yeasts.

For cooling towers, amounts of from 1 to 100 ppm, and for pulp and paper mills, amounts of from 50 to 500 ppm of a compound of the present invention are added to the pulp suspension in a paper mill or to the recirculating cooling water in a cooling tower in order to inhibit the growth of slime-forming bacteria, fungi, yeasts and algae.

For metal working fluids, i.e. cutting oils, amounts of from 200 to 2000 ppm of a compound of the present invention are added to a metal working fluid concentrate in order to inhibit the growth of bacteria, fungi, and yeasts during the use cycle of an oil-water lubricant for metal surfaces.

For other applications of the type described above, amounts of from 0.005 to 0.5% by weight, based on weight of the substrate being treated, of a compound of the present invention is incorporated into, sprayed onto, used to dip, or otherwise applied to the substrate to be treated in order to prevent growth of bacteria, fungi, yeasts, and algae.

The 1,2-dibromo-2-cyanoalkanes of the present invention may be prepared in accordance with a series of reactions which may be illustrated as follows:

(1) $$CH_2=CH-CH_2Br + Br_2 \xrightarrow{CCl_4} BrCH_2CH-CH_2$$
$$\phantom{CH_2=CH-CH_2Br + Br_2 \xrightarrow{CCl_4} BrCH_2CH} | \phantom{C} |$$
$$\phantom{CH_2=CH-CH_2Br + Br_2 \xrightarrow{CCl_4} BrCH_2CH} Br \phantom{C} Br$$
(II.)      (III.)

(2) $$BrCH_2CH-CH_2 \xrightarrow{NaOH} BrCH_2-C=CH_2$$
$$\phantom{BrCH_2C} | \phantom{H-} | \phantom{xxxxxxxxxxxxxx} |$$
$$\phantom{BrCH_2C} Br \phantom{H} Br \phantom{xxxxxxxxxxxxxxx} Br$$
(IV.)

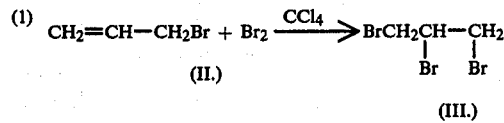

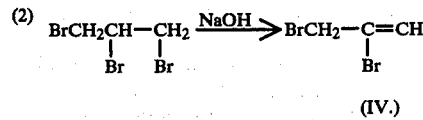

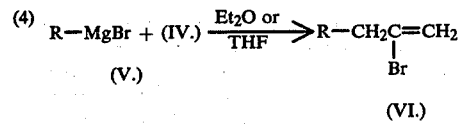

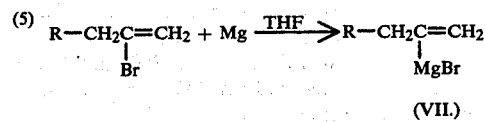

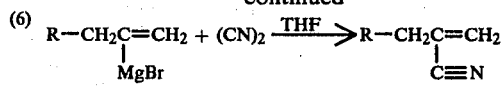

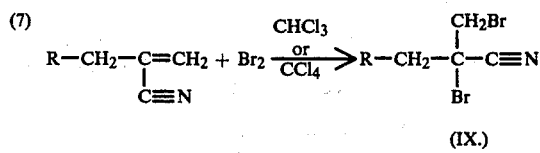

where R is as defined above.

In the first two steps shown above, the intermediate 2,3-dibromo-1-propane (IV.) is prepared from the available starting material 3-bromo-1-propene (II.) by bromination, followed by selective dehydrobromination with sodium hydroxide. The intermediate (IV.) is then reacted with a Grignard reagent (V.) containing the "R" substituent. The Grignard reagent is prepared in accordance with well-established techniques as shown in Step (3). After addition of the "R" group in Step (4), the bromine atom in the 2-position is converted to a cyano group by first reacting the intermediate (VI.) with magnesium, and the resulting intermediate (VII.) with cyanogen. Bromination of the intermediate (VIII.) gives the final product (IX.) which is a compound of Formula I where n is 1.

The following examples, which were actually carried out, will serve to further illustrate the present invention, without at the same time, however, constituting any limitation thereof.

EXAMPLE 1

Preparation of 1,2-dibromo-2-cyanopentane

A. 1,2,3-Tribromopropane

The reaction was carried out in a 5000 ml 3-necked round bottomed glass flask equipped with a motor-driven paddle stirrer, water-cooled reflux condenser, thermometer and a bromine addition funnel. The flask was charged with 605 g. of allyl bromide and 1250 ml of carbon tetrachloride. To this solution was added 1275 g of bromine at a rate so that the reaction temperature did not exceed 30° C. The addition was completed in about 20 hours after which time the solvent was stripped off to yield the theoretical amount of material as a heavy yellow oil. The product was used directly without further treatment in the next step.

B. 2,3-Dibromo-1-propene

A 1000 ml round bottomed flask was connected by a wide, bent glass adapter to an efficient condenser, which was provided with an adapter leading to a 500 ml receiving flask immersed in an ice bath. 600 g of 1,2,3-tribromopropane and 30 ml of water were charged to the reaction flask and 150 g of sodium hydroxide as pellets was added at once. Vigorous stirring was then provided by a magnetic stirrer, and the flask was heated with a heating mantle. Heat was applied until a vigorous boilind occured resulting in a spontaneous distillation of the reaction product. The mass became solid as the volatile products were removed. Heat was continued until no more product distilled.

The distillate in the receiving flask separated into two layers: an upper layer of water and a heavy layer of a colorless oil consisting of a mixture of the desired 2,3- dibromopropene and starting material. The distillate was transferred to a 500 ml separating funnel and the phases were separated. The organic phase was then washed with an additional 150 ml of water and dried overnight over anhydrous sodium sulfate. The crude product weighed 498 g. Fractional distillation under reduced pressure (56°–58° C./35 mm) gave 283 g. (66 percent of the theoretical amount). The residue consisted mainly of unreacted 1,2,3-tribromopropane which could be recycled to the next batch.

C. 2-Bromo-1-pentene

A 1000 ml 3-necked round-bottomed flask was fitted with a mechanical stirrer through a mineral oil sealed bearing, a reflux condenser and a 1000 ml addition funnel. A mixture of 203 g of 2,3-dibromopropane (1 mol) and 200 ml of dry ethyl ether was added. The flask was cooled to 0° C. in acetone/dry-ice and a solution of ethyl magnesium bromide, prepared from 31.0 g of magnesium, 136.3 g (1.25 mol) of ethylbromide, and 400 ml of dry ether was added at such a rate so that the temperature did not exceed 15° C. The addition took about 1 hour, 50 minutes. Stirring was continued and the acetone/dry-ice bath was replaced with a heating mantle. The mixture was gently refluxed for 1 hour, after which time the flask was again cooled and a solution of 15 ml 36% hydrochloric acid and 150 ml water was added dropwise by means of an addition funnel. The contents of the flask were then transferred to a separatory funnel, and the ether layer was separated and dried over anhydrous sodium sulfate. The ether was distilled off and the residue was fractionated under reduced pressure (100°–102° C./20 mm) yielding 42.5 g (29 percent of theory).

D. 2-Cyano-1-pentene

A 1000 ml 3-necked round-bottomed flask was fitted with a mechanical stirrer through a mineral oil sealed bearing, a reflux condenser, a thermometer, a 500 ml addition funnel, and a gas inlet tube (a static atmosphere of argon was maintained throughout the course of the reaction.) 150 ml of dry tetrahydrofuran was introduced and the flask was cooled to −10° C. in an acetone/dry-ice bath. The gas inlet tube was adjusted/dry-ice bath. The gas inlet tube was adjusted so that it extended beneath the surface of the tetrahydrofuran and 13.5 g of cyanogen was slowly bubbled in when the addition of gas was complete, the solution was stirred and a solution of 1-pentene-2-magnesium bromide, prepared from 42.5 g of 2-bromo-1-pentene prepared in Step C above; magnesium, and 400 ml of tetrahydrofuran, was slowly added. The addition took 2 hours and the temperature was regulated so that it did not exceed 0° C. When the addition was complete stirring was continued and the reaction was allowed to come to room temperature. After stirring for 2 hours the mixture was hydrolyzed by adding 150 ml of water and 5 ml of concentrated sulfuric acid. Two phases resulted, the separation of which improved after standing for several hours. The mixture was then transferred to a separatory funnel and the lower aqueous layer was separated from the organic phase. The aqueous layer was extracted with 300 ml of ethyl ether and combined with the organic layer which was then dried overnight over anhydrous sodium sulfate. After stripping off the solvents the residue was steam distilled to yield 2.6 g (9.5 percent of theory).

E. 1,2-Dibromo-2-cyanopentane

The reaction was carried out in a 250 ml 3-necked round bottomed flask equipped with a magnetic stirrer, water-cooled reflux condenser, thermometer and a bromine addition funnel. The flask was charged with 2.5 g of 2-cyano-1-pentene and 50 ml of dry chloroform. This solution 4.2 g of bromine was added and the mixture was stirred until the deep red color lightened. In this case the mixture was stirred for 18 hours. After stripping off the solvent, the crude material was purified by passing through silica gel to yield 4.3 g (64 percent of theory). Structure was confirmed by NMR.

EXAMPLES 2–6

The procedures of Example 1 were followed, substituting the appropriate Grignard reagent for the one employed therein, to prepare the compounds identified in the following table:

| Example No. | Grignard Reagent | Product $CH_2Br$ $\mid$ $R-C-C\equiv N$ $\mid$ $Br$ $R$ |
|---|---|---|
| 2 | $CH_3(CH_2)_5MgBr$ | $CH_3(CH_2)_6-$ |
| 3 | —MgBr | 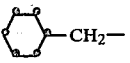—$CH_2-$ |
| 4 | $CH_3(CH_2)_7MgBr$ | $CH_3(CH_2)_8-$ |
| 5 | $(CH_3)_3CMgBr$ | $(CH_3)_3CCH_2-$ |
| 6 | $CH_3$ $\mid$ $CH_3(CH_2)_2CH-MgBr$ | $CH_3$ $\mid$ $CH_3(CH_2)_2CHCH_2$ |

EXAMPLES 7–10

In order to determine antimicrobial spectrum, the following techniques are employed:

Antibacterial Activity—A stock solution of the sample to be tested is prepared in 25% methanol. Dilutions of the stock solution are made into Tryptone Glucose Extract Agar (Difco) and the agar is poured into sterile petri dishes. After hardening, the plates are streaked with an aqueous suspension of the test organism. The inoculated plates are incubated at 35°–37° C. and examined after twenty-four hours for the presence or absence of growth. The lowest concentration at which no growth occurred is reported as the "Inhibiting Concentration".

Antifungal Activity—A stock solution of the sample to be tested is prepared in 25% methanol. Dilutions of the stock solution are made into Sabourand Maltose Agar (Difco) and the agar is poured into sterile petri dishes. After hardening, the plates are streaked with an aqueous spore suspension of the test organism. No wetting agent is used in preparation of the suspension. The inoculated plates are incubated at 28°–30° C. and examined after seven days for the presence or absence of growth. The lowest concentration at which no growth occurred, is reported as the "Inhibiting Concentration."

Employing the techniques described above, various of the 1,2-dibromo-2-cyanoalkanes of the present invention were tested at 10, 50, 100, 200, 400, 750, and 1000 ppm against the organisms, and with the results, indicated in the following table:

TABLE I

MINIMUM INHIBITORY CONCENTRATIONS (PPM)

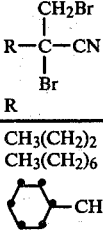

| Exp. No. | R | Aerobacter aerogenes | Pseudomonas aeruginosa | Aspergillus niger | Saccharomyces cerevisiae | Pullularia pullulans | Penicillium funiculosum | Alternaria brassicicola |
|---|---|---|---|---|---|---|---|---|
| 7 | $CH_3(CH_2)_2$ | 100 | 50 | 50 | 50 | 50 | 50/100 | 10 |
| 8 | $CH_3(CH_2)_6$ | 400 | 750 | 100 | 10 | 50/100 | 100/200 | 50 |
| 9 | ⌬—$CH_2$ | 100 | >1000 | 50 | 10 | 10 | 50 | 10 |
| 10 | $CH_3(CH_2)_8$ | >1000 | 1000 | 400 | 10 | 50 | 200 | 10 |

What is claimed is:

1. 1,2-dibromo-2-cyanononane.
2. 1,2-dibromo-2-cyano-3-cyclohexylpropane.
3. 1,2-dibromo-2-cyano-4-cyclooctylbutane.
4. 1,2-dibromo-2-cyanoundecane.
5. An antimicrobial composition comprising a carrier and an antimicrobially effective amount of a compound selected from the group consisting of 1,2-dibromo-2-cyanononane; 1,2-dibromo-2-cyano-3-cyclohexylpropane; 1,2-dibromo-2-cyano-4-cyclooctylbutane; and 1,2-dibromo-2-cyanoundecane.
6. A method of inhibiting the growth of microorganisms, comprising contacting said microorganism with an antimicrobially effective amount of a compound selected from the group consisting of 1,2-dibromo-2-cyanononane; 1,2-dibromo-2-cyano-3-cyclohexylpropane; 1,2-dibromo-2-cyano-4-cyclooctylbutane; and 1,2-dibromo-2-cyanoundecane.
7. A method of inhibiting the growth of microorganisms in pulp and paper mill systems, comprising incorporating into the mass of fiber and water in such a pulp and paper mill system so as to contact said microorganism with an antimicrobially effective amount of a compound selected from the group consisting of 1,2-dibromo-2-cyanononane; 1,2-dibromo-2-cyano-3-cyclohexylpropane; 1,2-dibromo-2-cyano-4-cyclooctylbutane; and 1,2-dibromo-2-cyanoundecane.
8. A composition according to claim 5 wherein the carrier is a petroleum distillate fraction.
9. A composition according to claim 5 wherein the carrier is a finely divided solid.
10. A method of inhibiting growth of microorganisms in latex compositions or metal working fluids comprising incorporating in said latex compositions or metal working fluids an antimicrobially effective amount of a compound selected from the group consisting of 1,2-dibromo-2-cyanononane; 1,2-dibromo-2-cyano-3-cyclohexylpropane; 1,2-dibromo-2-cyano-4-cyclooctylbutane; and 1,2-dibromo-2-cyanoundecane.

* * * * *